(12) United States Patent
Halkias et al.

(10) Patent No.: US 9,107,614 B2
(45) Date of Patent: Aug. 18, 2015

(54) SYSTEMS, METHODS, AND MEDIA FOR FINDING AND MATCHING TREMOR SIGNALS

(76) Inventors: Xanadu Christina Halkias, New York, NY (US); Henry Frisz, Huntington, NY (US)

(*) Notice: Subject to any disclaimer, the term of this patent is extended or adjusted under 35 U.S.C. 154(b) by 918 days.

(21) Appl. No.: 13/180,865

(22) Filed: Jul. 12, 2011

(65) Prior Publication Data

US 2013/0018283 A1  Jan. 17, 2013

(51) Int. Cl.
| | |
|---|---|
| A61B 5/103 | (2006.01) |
| A61B 5/117 | (2006.01) |
| A61B 5/11 | (2006.01) |
| A61B 5/00 | (2006.01) |

(52) U.S. Cl.
CPC ............. *A61B 5/1101* (2013.01); *A61B 5/4082* (2013.01); *A61B 5/7235* (2013.01)

(58) Field of Classification Search
CPC ... A61B 5/7235; A61B 5/4082; A61B 5/1101
USPC .............................. 600/300, 587–595; 702/19
See application file for complete search history.

(56) References Cited

U.S. PATENT DOCUMENTS

| | | | |
|---|---|---|---|
| 5,058,571 A | 10/1991 | Hall | |
| 5,368,042 A | 11/1994 | O'Neal et al. | |
| 5,643,332 A | 7/1997 | Stein | |
| 6,081,744 A | 6/2000 | Loos | |
| 6,379,313 B1 | 4/2002 | Gozani et al. | |
| 6,458,089 B1 | 10/2002 | Ziv-Av | |
| 6,695,794 B2 | 2/2004 | Kaiser et al. | |
| 6,730,049 B2 | 5/2004 | Kalvert | |
| 6,839,594 B2 | 1/2005 | Cohen et al. | |
| 6,936,016 B2 * | 8/2005 | Berme et al. | 600/595 |
| 7,369,896 B2 | 5/2008 | Gesotti | |

(Continued)

FOREIGN PATENT DOCUMENTS

| | | |
|---|---|---|
| DE | 102008042373 | 4/2010 |
| WO | WO 2005/011494 | 2/2005 |

(Continued)

OTHER PUBLICATIONS

Burn, J.A., et al., "Muscle Loading as a Method to Isolate the Underlying Tremor Components in Essential Tremor and Parkinson's Disease", In Muscle Nerve vol. 30, No. 3, Sep. 2004, pp. 347-355.

(Continued)

*Primary Examiner* — Max Hindenburg
*Assistant Examiner* — Jonathan M Foreman
(74) *Attorney, Agent, or Firm* — Xanadu C. Halkias

(57) ABSTRACT

System, methods, and media for finding and matching tremor signals that: receive a first piece of tremor signal content; identify a first plurality of tremor peaks that describe at least a portion of the first piece of tremor signal content using a Teager-Kaiser operator; form a first template of tremor peaks from at least a portion of the first plurality of tremor peaks, the first group of tremor peaks having a first croup of parameters; compare the first template and the first group of parameters with at least one second template and a second group of parameters, wherein the second group of parameters is based on a second set of tremor peaks associated with a second piece of tremor content; and identify a match between the first piece of tremor signal content and the second piece of tremor signal content based on the comparing.

8 Claims, 4 Drawing Sheets

(56) References Cited

U.S. PATENT DOCUMENTS

| | | | |
|---|---|---|---|
| 7,489,973 | B2 | 2/2009 | Shah |
| 7,643,882 | B2 | 1/2010 | Boston |
| 7,959,578 | B2 * | 6/2011 | Lonky .......................... 600/558 |
| 2002/0107556 | A1 | 8/2002 | McIoul et al. |
| 2007/0106343 | A1 | 5/2007 | Monogue et al. |
| 2007/0112394 | A1 | 5/2007 | Nathan et al. |
| 2007/0129771 | A1 | 6/2007 | Kurtz et al. |
| 2008/0167583 | A1 | 7/2008 | Meir et al. |
| 2009/0005713 | A1 | 1/2009 | Podranzhansky et al. |
| 2009/0149919 | A1 | 6/2009 | Dacey, Jr. et al. |
| 2010/0198115 | A1 | 8/2010 | Koeneman et al. |
| 2010/0211122 | A1 | 8/2010 | Hensley |
| 2010/0249662 | A1 | 9/2010 | Shimizu |

FOREIGN PATENT DOCUMENTS

| | | |
|---|---|---|
| WO | WO 2005/020866 | 3/2005 |
| WO | WO 2006/064074 | 6/2006 |
| WO | WO 2008/096031 | 8/2008 |

OTHER PUBLICATIONS

Forssberg, H., et al., "Action Tremor During Object Manipulation in Parkinson's Disease", In Movement Disorders, vol. 15, No. 2, Mar. 2000, pp. 244-254.

Hurtado, J.M., et al., "Temporal Evolution of Oscillations and Synchrony in GPi/Muscle Pairs in Parkinson's Disease", In Journal of Neurophysiology, vol. 93, Mar. 2005, pp. 1569-1584.

Kim, S. and McNames, J., "Tracking Tremor Frequency in Spike Trains Using the Extended Kalman Filter", In Proceedings of the 27th Annual IEEE Engineering in Medicine and Biology Conference, Shanghai, CN, Sep. 1-4, 2005.

Lauk, M., et al., "Side-to-Side Correlation of Muscle Activity in Physiological and Pathological Human Tremors", In Clinical Neurophysiology, vol. 110, No. 10, Oct. 1999, pp. 1774-1783.

Lee, R.G., and Stein, R.B., "Resetting of Tremor by Mechanical Perturbations: A Comparison of Essential Tremor and Parkinsonian Tremor", In Annals of Neurology, vol. 10, No. 6, Dec. 1981, pp. 523-531.

Lenz, F.A., et al., "Single Unit Analysis of the Human Ventral Thalamic Nuclear Group: Correlation of Thalamic 'Tremor Cells' with the 3-6 Hz Component of Parkinsonian Tremor", In the Journal of Neuroscience, vol. 8, No. 3, Mar. 1988, pp. 754-764.

Levy, R., et al., "High-Frequency Synchronization of Neuronal Activity in the Subthalamic Nucleus of Parkinsonian Patients with Limb Tremor", In the Journal of Neuroscience, Oct. 15, 2000, vol. 20, No. 20, pp. 7766-7775.

McAuley, J.H., et al., "Frequency Peaks of Tremor, Muscle Vibration and Electromyographic Activity at 10Hz, 20Hz and 40Hz During Human Finger Muscle Contraction May Reflect Rythmicities of Central Neural Firing", In Experimental Brain Research, vol. 114, No. 3, May 1997, pp. 525-541.

Milanov, I., "A Cross-Over Clinical and Electromyographic Assessment of Treatment for Parkinsonian Tremor", In Parkinsonism and Related Disorders, vol. 8, No. 1, Sep. 2001, pp. 67-73.

O'Suilleabhain, P.E. and Matsumoto, J.Y., "Time-Frequency Analysis of Tremors", In Brain, vol. 121, No. 11, Nov. 1998, pp. 2127-2134.

Suzuki, H., et al., "Relationships Between Surface-Detected EMG Signals and Motor Unit Activation", In Medicine and Science in Sports and Exercise, vol. 34, No. 9, Sep. 2002, pp. 1509-1517.

* cited by examiner

SYSTEMS, METHODS, AND MEDIA FOR FINDING AND MATCHING TREMOR SIGNALS

TECHNICAL FIELD

The disclosed subject matter relates to systems, methods, and media for finding and matching tremor signals.

BACKGROUND

Movement disorders such as Parkinson's disease have been increasingly affecting larger and younger portions of the global population. These disorders are usually associated with degeneration of the central nervous system. The most common symptoms surrounding Parkinson's disease are movement related and include most notably shaking, rigidity, slowness of movement and difficulty with walking and gait.

Parkinsonian tremor has long been accepted as the most distinct symptom that indicates the presence of the disease and its severity, and also serves as a measure of the progress and evolution of the disease. Most Parkinson's patients find that the most difficult part of the disease is the induced tremor attributed mainly to the lack of dopamine in the brain. Research has introduced two main types of tremors that affect most Parkinson's patients: (i) resting tremor, which occurs when an individual is resting and can inhibit activities such as sleeping; and (ii) action tremor, which occurs when an individual is performing a specific task such as lifting an object.

Tremor signals are a result of the lack of dopamine in a patient's brain, leading to errors regarding the transmission of electrical nerve impulses through the patient's central and peripheral nervous systems. These transmission errors, appear as involuntary, rapid movements that generally affect a person's limbs (e.g., arms, hands, feet, etc.). Tremor signals are typically measured using electromyograms (EMG), accelerometers, etc.

The most current advances in medicine and science regarding alleviating Parkinson's tremors can be classified into two main categories: firstly, pharmaceutical options that aim to balance the amount of dopamine in the brain and that can cause known side effects such as painful rigidity; and secondly, the use of deep brain implants that stimulate areas of the brain responsible for motor movement. However, pharmaceutical options and deep brain implants can have an inherent danger attached to them due to the process and surgery required to place them in the brain as well as the fact that currently, the medical community does not have an understanding of the causes and origin of Parkinson's disease.

Accordingly, new, non-invasive, and non-pharmaceutical driven, techniques for managing tremors are needed.

SUMMARY

In accordance with some embodiments, systems, methods, and media for finding and matching tremor signals are provided. Such systems, methods, and media can be used to compare tremor signals for the purposes of categorizing pathological and physiological tremors, removing and cancelling-out identified tremor signals, identifying similar tremors, identifying multiple tremors in long recordings, etc.

In some embodiments, systems for finding and matching tremor signals are provided, the systems comprising: at least one processor that: receives a first piece of tremor signal content, identifies a first plurality of tremor peaks that describe at least a portion of the first piece of tremor signal content using a Teager-Kaiser operator; forms a first template of tremor peaks from at least a portion of the first plurality of tremor peaks, the first template of tremor peaks having first group parameters; compares the at least one first template and its parameters with at least one second template and its parameters, wherein the at least one second group of parameters is based on a second set of tremor peaks associated with a second piece of tremor content; and identifies a match between the first piece of tremor signal content and the second piece of tremor signal content based on comparing.

In some embodiments, methods for finding and matching tremor signals are provided, the methods comprising: receiving a first piece of tremor signal content; identifying a first plurality of tremor peaks that describe at least a portion of the first piece of tremor signal content using a Teager-Kaiser operator; forming a first template of tremor peaks from at least a portion of the first plurality of tremor peaks, the first template of tremor peaks having first group parameters; comparing the at least one first template and its parameters with at least one second template and group of parameters, wherein the at least one second group of parameters is based on a second set of tremor peaks associated with a second piece of tremor content; and identifying a match between the first piece of tremor signal content and the second piece of tremor signal content based on the comparing.

In some embodiments, computer readable media containing computer executable instructions that when executed by at least one processor cause the processor to perform a method for finding and matching tremor signals are provided, the method comprising: receiving a first piece of tremor signal content, identifying a first plurality of tremor peaks that describe at least a portion of the first piece of tremor signal content using a Teager-Kaiser operator; forming a first template of tremor peaks from at least a portion of the first plurality of tremor peaks, the first template of tremor peaks having first group parameters; comparing the at least one first template and its parameters with at least one second template and group of parameters, wherein the at least one second group of parameters is based on a second set of tremor peaks associated with a second piece of tremor content; and identifying a match between the first piece of tremor signal content and the second piece of tremor signal content based on the comparing.

DETAILED DESCRIPTION

Movement disorders such as Parkinson's disease can exhibit several symptoms. One of the most distinct symptoms is the appearance of involuntary limb movements known as tremors that can severely inhibit a patient's mobility and that are caused by tremor signals from the brain due to the lack of dopamine in a patient's brain.

In accordance with some embodiments, systems, methods and media for identifying and matching tremor signals are presented that can provide a non-invasive approach in arresting and managing tremor signals.

In order to perform such functions, tremor signals can be measured using several monitoring apparatus such as an electromyogram (EMG), an accelerometer or any other suitable device. In order to describe one or more portions of a tremor signal, unique tremor peak sequences can then be identified and used to form templates of tremor signal content. In some embodiments, and depending on the tremor monitoring apparatus, these peaks can be peaks in the rate of change of the tremor signal, peaks in the amplitude of the tremor signal and/or peaks in any other suitable form of tremor measurement. Unwanted peaks can be removed from further processing through the use of pruning. Depending on the identified peaks, sets of peaks can next be formed. A set of unique tremor peaks at a specific instance in time may be considered to be a descriptor of a given tremor signal and may be used as a template. These sets of peaks can then be stored in a database and can take the form of a table or vector space. Upon storage in the database, these tremor peak sets can be used as templates to identify matching tremors from the same tremor source and/or a different tremor source that can be obtained in different times. Once a match is identified, the template can be used to create a new signal and/or output that can minimize and/or cancel the tremor signal.

Figure 3:
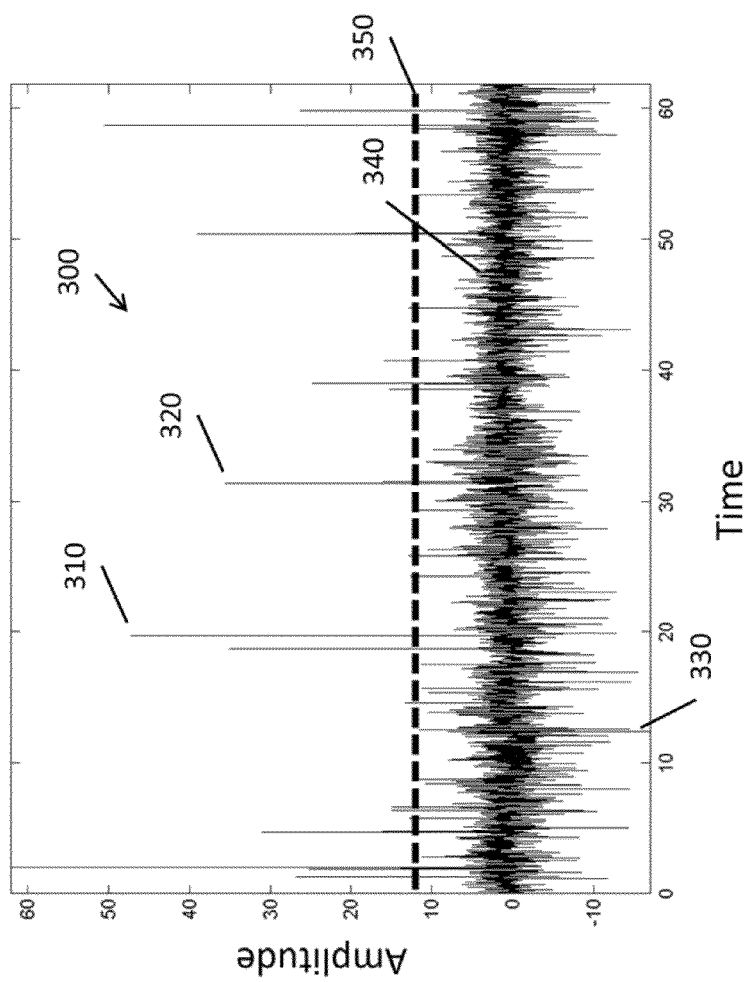
FIG. 3 is a diagram of a tremor signal and its components that can be identified in accordance with some embodiments.

FIG. 3 depicts an example of a tremor signal 300 in accordance with some embodiments. Components 310, 320, and 330 indicate tremor peaks that can be grouped together to form a template. Each tremor peak represents an involuntary limb movement in a specific direction. For example, tremor peak 310 indicates that the limb movement is occurring in the opposite direction of the movement represented by tremor peak 330. Component 340 illustrates background interference such as physiological tremor and/or additive noise from the recording apparatus, etc., which can be present when identifying tremor peaks. Threshold 350 can be used for pruning the identified tremor peaks in order to minimize the background interference.

Figure 1A:
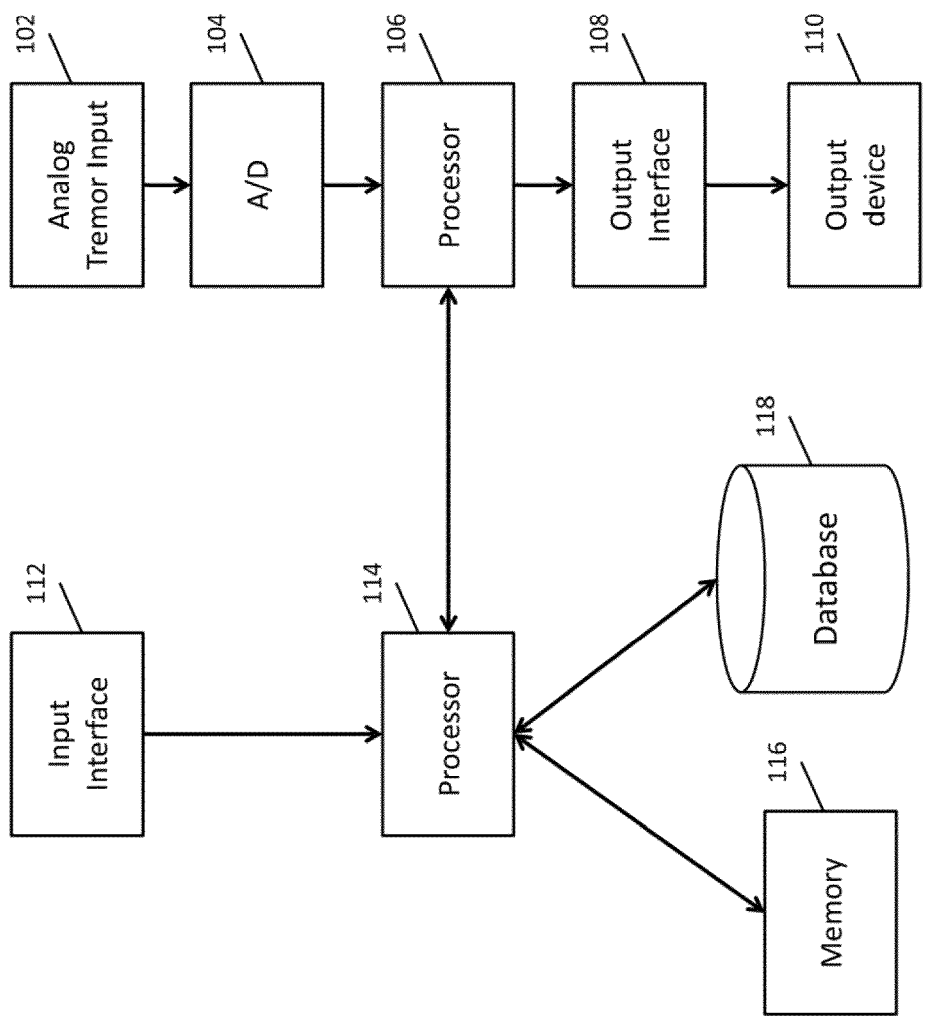
FIG. 1A is a diagram of one configuration of hardware that can be used in accordance with some embodiments.

FIG. 1A illustrates an example of hardware 100. As depicted, hardware 100 can include an analog tremor signal input 102, an analog-to-digital converter 104, a first processor 106, an output interface 108, an output device 110, an input interface 112, a second processor 114, memory 116, and a database 118. Inputs 102 can be formed by any suitable input for receiving tremor signals, such as an accelerometer, an electromyogram (EMG), a storage medium (such as an analog or digital storage medium), etc. Analog-to-digital converter 104 can be any suitable converter for converting an analog signal to digital form, and can include a converter having any suitable resolution, sampling rate, input amplitude range, etc. Input interface 112 can be any suitable input interface for receiving tremor signal content in a digital form, such as a network interface, a USB interface, a serial interface, a parallel interface, a storage device interface, an optical interface, a wireless interface, etc. First processor 106, and second processor 114 can include any suitable processing devices such as computers, servers, microprocessors, controllers, digital signal processors, programmable logic devices, etc. Instructions (e.g., software, firmware etc.) for controlling such processors can be stored on any suitable computer readable media, such as disk drives, compact disks, digital video disks, memory (such as random access memory, read only memory, flash memory, etc.), and/or any other suitable media. Memory 116 can include any suitable computer readable media, such as disk drives, compact disks, digital video disks, memory (such as random access memory, read only memory, flash memory, etc.), and/or any other suitable media, and can be used to store instructions for performing the processes described herein such as that described in connection with FIG. 2. Database 118 can include and suitable hardware and/or software database for storing data. Output interface 108 can include any suitable interface for providing data to an output device, such as a video display interface, a network interface, an amplifier, etc. The indicators of found tremor events, or one or more of such events, can be coupled to output devices using any suitable interface. For example, such indicators can be displayed on display screens though a video interface, such indicators and/or event(s) can be provided to network devices through a network interface and/or to electro-mechanical devices (such as piezoelectric materials) through an amplifier, etc. Output device 110 can include any suitable device for outputting data and can include display screens, network devices, electro-mechanical devices, etc. In some embodiments, output device 110 can be an external, adjustable device that can arrest and/or cancel the tremor signal using vibrations, pressure, electrical pulses or any other suitable electromechanical output.

Hardware 100 can be implemented in any suitable form. For example, hardware 100 can be implemented as a Web server, including one or more hardware processors, that receives a potential tremor signal from a user, analyzes the signal, and provides identifiers for matching tremors to the user. As other examples, hardware 100 can be implemented as a combination of a user computer and a wearable, portable signal recorder/player, a camera, a mobile phone, a tablet computing device, an email device, etc. that receives a potential tremor signal from a user, analyzes the signal, provides identifiers for matching tremors to the user, and outputs a signal that can arrest and/or cancel the tremor signal based on the identified matching tremors. In some embodiments the output signal can be a vibration at a specified frequency, and/or electrical pulses, and/or pressure and/or any other suitable form of force with the ability to effectively minimize and/or cancel a tremor signal.

Figure 1B:
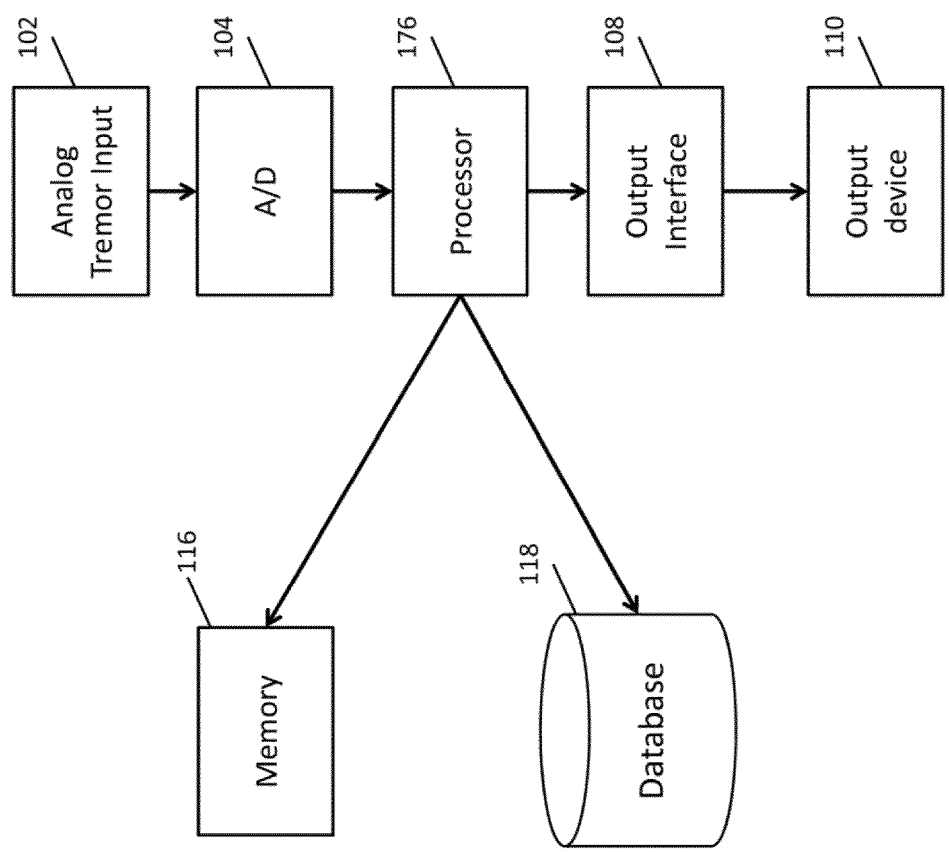
FIG. 1B is a diagram of another configuration of hardware that can be used in accordance with some embodiments.

FIG. 1B shows an alternate configuration of hardware 170 that can be used to implement some embodiments of the present invention. Components 102, 104, 108, 110, 116, and 118 in FIG. 1B can be substantially the same as components 102, 104, 108, 110, 116, and 118 in FIG. 1A. Processor 176 in FIG. 1B can perform a combination of the functions of processors 106, and 114 shown in FIG. 1A. In some embodiments, hardware 170 can be implemented as a wearable, portable device that receives a potential tremor signal from the user, analyzes the signal, provides identifiers for matching tremors to the user and generates a force that can arrest and/or cancel the tremor signal.

Figure 2:
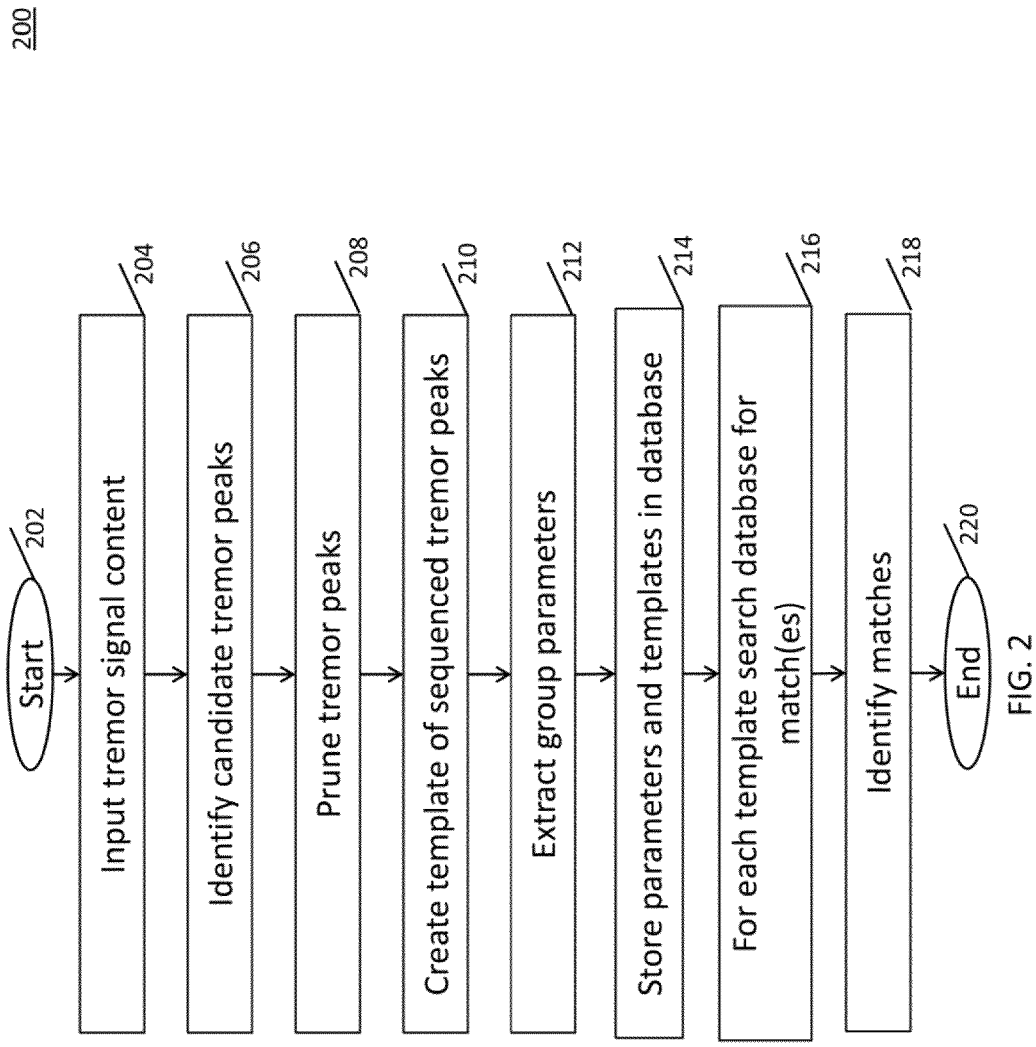
FIG. 2 is a diagram of a process for identifying and matching tremor signals that can be used in accordance with some embodiments.

In FIG. 2, a process 200 for identifying and matching identical and/or similar tremor signals is illustrated. The process starts at 202 and subsequently receives as input the tremor signal content at 204. Step 204 can be performed by components 112 and/or 102 and 104 of hardware 100. The tremor signal content can have matching intra-signal tremor instances (e.g., matching tremor signals within the same signal content) or matching inter-signal tremor instances (e.g., matching tremor signals in different signal content).

Receipt of the tremor signal content can be achieved in multiple ways. For example, the tremor content can be received in digital format as a digital file (e.g., a ".txt" file, an ".xml" file, etc.), as a digital stream, as digital content in a storage device (e.g., memory, a database, etc.). As another example, the tremor content can be received as an analog signal, which is then converted to digital format using an analog to digital converter. Such an analog signal can be received through an electromyogram, an accelerometer, etc.

Next, at 206, process 200 can identify peaks that can possibly describe the tremor content. A set of peaks that is descriptive of the signal tremor content can be classified as a template. Each template can also have identifiable parameters that can define for example, a template's peak frequency, amplitude, length, and/or any other suitable characteristic(s) that can be associated to the type of tremor (e.g., action tremor, resting tremor, etc.)

In some embodiments, these sets of peaks can be obtained using the discrete Teager-Kaiser (TK) operator. As is known in the art, the Teager-Kaiser operator is a non-linear, quadratic operator introduced to measure the real physical energy of a system. This operator differs from the traditional way of measuring the energy of a signal by suppressing unwanted background noise and highlighting candidate tremor peaks. The discrete time TK operator for real valued tremor signals can be given by:

$$E_D[x(n)] = E(n) = x^2(n) - x(n-1)*x(n+1)$$

As another example, in some embodiments, the discrete TK operator can be used in windowed portions of the tremor signal content. Temporal windowing of the tremor signal can provide a faster, more-efficient and more-sensitive method for identifying the tremor peaks. Examples of temporal windows can vary. In some embodiments, initial windows can range anywhere from half a second to two seconds, although any suitable temporal windows can be used.

Tremor peaks cam be pruned using a temporal window. For example, in some embodiments, temporal windowing can be combined with half-wave rectification of the discrete Teager-Kaiser operator which takes advantage of the symmetric nature of the tremor signal and also minimizes the need for using multiple thresholds. Denoising filters such as moving average filters or any other suitable filters may be used in combination with the TK operator to increase the sensitivity of identifying candidate tremor peaks.

In some embodiments, temporal windowing can be used and repeated with different sized windows in order to achieve different resolutions of analysis. For example, after the tremor signal content is analyzed in a given time window the same analysis can be repeated in a smaller or larger time window to increase or decrease, respectively, the sensitivity and accuracy in identifying the tremor peaks.

After identifying tremor peaks in 206, process 200 can then prune tremor peaks at 208 in some embodiments.

Tremor peaks may need to be pruned, for example, because when peaks are identified using the discrete TK operator, there is a possibility of also identifying non-tremor peaks (e.g., physiological tremor peaks). On average, a person suffering from Parkinson's disease will exhibit an action tremor (e.g., involuntary movement when performing an intentional action) or a resting tremor (e.g., involuntary movement when resting), or a combination of both. These tremors can appear as peaks in the tremor content signal. The set of these tremor peaks can be unique for each individual. The frequency of the tremor peaks can occur with a range of 4 Hertz-6 Hertz, or any other suitable frequency range.

In some embodiments, one can initially use a temporal window of one second length for analyzing and identifying tremor signal content to be pruned. Using the rectified discrete TK operator, one can then calculate the probability density function of the tremor peaks by forming a histogram of the resulting signal. Once the histogram has been obtained, one can choose to use those bins of the histogram that contain less than six peaks but at least one peak or any other suitable characteristic as a way to identify a threshold for pruning. Once the minimum value of a potential candidate tremor peak is selected, it can be used as a threshold in the original tremor signal content to obtain a first initial set of pruned tremor peak candidates. In some embodiments multiple thresholds can be used for different portions of the tremor signal content.

In some embodiments, one can provide an additional layer of pruning of already-identified candidate tremor peaks by using a multi-resolution approach. For example in doing so, the already-identified candidate tremor peaks can be further pruned by using a larger temporal window for analysis. More particularly, for example, one can use a two-second temporal window and then only keep the twelve highest peaks as the final tremor peaks or any other suitable number of peaks.

In some embodiments, one can chose different temporal windows for the analysis and identification of the tremor peaks for pruning. Multiple instances of temporal windows at different sizes can also be added, which can increase the sensitivity and specificity of the pruning process.

As a result of pruning the candidate tremor peaks at 208, a set of unique sequenced tremor peaks can be obtained. At 210, this set of unique sequenced tremor peaks can be grouped to any suitable temporal arrangement to form a template. In some embodiments, such temporal arrangements can represent, for example, different time frames (e.g., a resting tremor template can represent a patient's set of tremor peaks during sleep). In some embodiments these temporal arrangements can represent, for example, different actions (e.g., a writing tremor template can represent a patient's set of tremor peaks during an attempt to write).

Each set of tremor peaks that forms a template can have descriptive parameters. Such set parameters can include, for example, the frequency of occurrence, the first order or second order inter-peak distance, the amplitude of the peaks, etc. These parameters can be extracted at 212. In some embodiments, energy levels can be obtained and/or any other suitable characteristic can also be included as part of the extracted set of parameters.

Theses parameters along with the templates of tremor peaks can then be stored in a database (or any other suitable storage mechanism) at 214. This database can also contain parameters and other templates previously stored during other iterations of process 200 for other tremor signal content.

At 216, matches between tremor signals can be obtained by searching through the database and identifying similar and/or identical matches between different templates.

Step 218 of process 200 can identify matches between tremor signals. Matching tremor signals can be identified by either comparing directly the different templates or by identifying those templates that share common parameters. These parameters can either be the same or their values can fall within a predetermined range. This range can be either manually or automatically set based on the number of tremor peaks and their frequency of occurrence. In some embodiments, identical or similar content can also be identified using the stored set of tremor peaks. Identical or similar sets of tremor peaks and/or corresponding parameters can be referred to as matching tremor signals. In some embodiments, real time or near real time identification of tremor peaks can be performed In some embodiments, the comparison can be achieved by the use of a cross-correlation coefficient calculated between the stored set of tremor peaks and the new tremor signal content. Such a cross-correlation coefficient represents the similarity between the template and the new tremor signal content.

In some embodiments, the comparison at step 218 can be performed using matched filtering. A matched filter can be used to correlate a known signal/template with an unknown signal to detect the presence of the template in the signal. The matched filter can be a linear filter that maximizes the signal to noise ratio in the presence of additive noise in some embodiments.

In some embodiments, tremor signal content recordings can be obtained and analyzed off-line to create and learn individual tremor models. These tremor models can be the result of generative approaches such as Hidden Markov Models or Gaussian Mixture Models. Once these models are created, the extracted parameters from the tremor signal can be used to identify the likelihood of an unknown tremor signal matching existing tremor signals stored in the database as shown in step 218.

In some embodiments, discriminative learning can be used to identify tremor peaks in an unknown tremor signal content as depicted in 218. For example, Support Vector Machines, Neural Networks and other suitable techniques can be trained using the parameters and sets of tremor peaks stored in the database. An unknown signal can then be evaluated by the models and its peaks can be determined to be tremor peaks or not.

Steps 206-218 of process 200 can occur in either or both of the two processors depicted in hardware 100 (106, 114).

Finally, at 220, the device can generate an anti-tremor force. This force can be a vibration at a specified frequency obtained from the matching template, and/or electrical pulses, and/or pressure and/or any other suitable form of force with the ability to effectively minimize a patient's tremor signal. In some embodiments, an adjustable, inflatable band may be used to apply pressure based on parameters obtained from the matching template. In some embodiments, a band can have an electromechanical circuit including a piezoelectric transducer and an amplifier, and/or any other suitable combination of electromechanical circuit, that results in the generation of anti-tremor force.

In some embodiments, the techniques used to identify matching tremor signals in recordings can be used for any suitable application. For example, in some embodiments, these techniques can be used to identify a repeating tremor in a single recording. As another example, in some embodiments these techniques can be used to identify a similar or identical tremor peak or set of tremor peaks in two or more signals. As yet another example, in some embodiments, these techniques can be used to identify two or more sets of tremor peaks as being recorded during a single temporal window based on matching tremor content in the sets.

In some embodiments, any suitable computer-readable media can be used for storing instructions for performing the functions described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims which follow. Features of the disclosed embodiments can be combined and rearranged in various ways.

What is claimed is:

1. A system for finding and matching tremor signals comprising:
    a hardware sensor capable of measuring an analog tremor signal;
    an analog to digital converter, coupled to the hardware sensor, that converts the analog tremor signal into a digital tremor signal;
    a piezoelectric transducer capable of receiving the digital tremor signal;
    at least one hardware processor coupled to the analog to digital converter and the piezoelectric transducer that:
        receives a first piece of the digital tremor signal;
        identifies a first plurality of tremor peaks that describe at least a portion of the first piece of digital tremor signal using a Teager-Kaiser operator;
        forms a first template of tremor peaks from at least a portion of the first plurality of tremor peaks, the first template of tremor peaks having a first group of parameters;
        stores the first template of tremor peaks and the first group of parameters in an electronic storage device;
        compares the first template and the first group of parameters with at least one second template and a second group of parameters, wherein the second group of parameters is based on a second set of tremor peaks associated with a second piece of digital tremor signal;
        identifies a match between the first piece of digital tremor signal and the second piece of digital tremor signal based on the comparing; and
        causes the piezoelectric transducer to generate a mechanical movement based on the second template of tremor peaks and the second group of parameters.

2. The system of claim 1, wherein the first piece of digital tremor signal and the second piece of digital tremor signal are from a single recording.

3. The system of claim 1, wherein the processor also applies temporal windowing on the tremor signal.

4. The system of claim 1, wherein comparing is obtained through template matching.

5. The system of claim 1, wherein the processor also prunes the first plurality of tremor peaks after identifying the first plurality of tremor peaks and before forming of the first template of tremor peaks.

6. The system of claim 5, wherein pruning is based on at least one threshold.

7. The system of claim 5, wherein pruning is repeated using a different temporal window.

8. A computer-readable medium containing computer-executable instructions that, when executed by at least one hardware processor that is coupled to an analog to digital converter and a piezoelectric transducer, cause the at least one hardware processor to perform a method for finding and matching tremor signal content, the method comprising:
    receiving a first piece of a digital tremor signal;
    identifying a first plurality of tremor peaks that describe at least a portion of the first piece of the digital tremor signal using a Teager-Kaiser operator;

forming a first template of tremor peaks from at least a portion of the first plurality of tremor peaks, the first template of tremor peaks having a first group of parameters;

forming the first template of tremor peaks and the first group of parameters in an electronic storage device;

comparing the first template and the first group of parameters with at least one second template and a second group of parameters, wherein the second group of parameters is based on a second set of tremor peaks associated with a second piece of digital tremor signal;

identifying a match between the first piece of digital tremor signal and the second piece of digital tremor signal based on the comparing; and causing the piezoelectric transducer to generate a mechanical movement based on the second template of tremor peaks and the second group of parameters.

* * * * *